(12) United States Patent
Yu et al.

(10) Patent No.: US 9,644,003 B2
(45) Date of Patent: May 9, 2017

(54) RTN4B POLYPEPTIDE, MONOCLONAL ANTIBODY THEREOF, MONOCLONAL ANTIBODY-PRODUCING HYBRIDOMA CELL STRAIN, AND, PREPARATION AND APPLICATION THEREOF

(71) Applicant: FUDAN UNIVERSITY, Shanghai (CN)

(72) Inventors: Long Yu, Shanghai (CN); Guoqing Ji, Shanghai (CN); Dingding Han, Shanghai (CN); Yanhua Wu, Shanghai (CN); Lisha Tang, Shanghai (CN)

(73) Assignee: FUDAN UNIVERSITY, Yangpu District, Shanghai (CN)

( * ) Notice: Subject to any disclaimer, the term of this patent is extended or adjusted under 35 U.S.C. 154(b) by 0 days.

(21) Appl. No.: 14/397,539

(22) PCT Filed: May 6, 2013

(86) PCT No.: PCT/CN2013/075184
§ 371 (c)(1),
(2) Date: Oct. 28, 2014

(87) PCT Pub. No.: WO2013/166943
PCT Pub. Date: Nov. 14, 2013

(65) Prior Publication Data
US 2015/0125885 A1    May 7, 2015

(30) Foreign Application Priority Data

May 8, 2012    (CN) .......................... 2012 1 0141101
May 29, 2012    (CN) .......................... 2012 1 0171629

(51) Int. Cl.
| | | |
|---|---|---|
| *C07K 7/08* | (2006.01) | |
| *C07K 14/47* | (2006.01) | |
| *C07K 16/18* | (2006.01) | |
| *C12N 5/16* | (2006.01) | |
| *G01N 33/574* | (2006.01) | |
| *C07K 16/22* | (2006.01) | |
| *A61K 38/00* | (2006.01) | |
| *A61K 39/00* | (2006.01) | |

(52) U.S. Cl.
CPC ................ *C07K 7/08* (2013.01); *C07K 14/47* (2013.01); *C07K 16/18* (2013.01); *C07K 16/22* (2013.01); *C12N 5/16* (2013.01); *G01N 33/57496* (2013.01); *A61K 38/00* (2013.01); *A61K 2039/505* (2013.01); *C07K 2317/54* (2013.01); *C07K 2317/55* (2013.01); *C07K 2317/76* (2013.01)

(58) Field of Classification Search
None
See application file for complete search history.

(56) References Cited

U.S. PATENT DOCUMENTS

2009/0232822 A1* 9/2009 Joseloff ............ G01N 33/57423
424/139.1

OTHER PUBLICATIONS

Yu et al, CN101017166 A, Chines Patent application published on Aug. 2007.*
He et al, Nature Medcine, 10: 959-965, 2004.*
Colman et al, Research in Immunology, 1994; 145(1): 33-36.*
Abaza et al, Journal of Protein Chemistry, vol. 11, No. 5, 1992, pp. 433-444, abstract.*

* cited by examiner

*Primary Examiner* — Lei Yao
(74) *Attorney, Agent, or Firm* — Global IP Services; Tianhua Gu

(57) ABSTRACT

The present invention relates to a RTN4B-related polypeptide, a monoclonal antibody thereof, a monoclonal antibody-producing hybridoma cell strain, and, preparation and applications thereof. The RTN4B polypeptide comprises an amino acid sequence presented by SEQ ID NO: 1. The invention further discloses a monoclonal antibody, a hybridoma cell strain to produce the monoclonal antibody prepared by the RTN4B polypeptide, and the related application in the treatment or prevention of tumors thereof.

14 Claims, 2 Drawing Sheets

RTN4B POLYPEPTIDE, MONOCLONAL ANTIBODY THEREOF, MONOCLONAL ANTIBODY-PRODUCING HYBRIDOMA CELL STRAIN, AND, PREPARATION AND APPLICATION THEREOF

CROSS REFERENCE TO RELATED PATENT APPLICATION

The present application is the US national stage of PCT/CN2013/075184 filed on May 6, 2013, which claims the priorities of the Chinese patent applications No. 201210141101.1 filed on May 8, 2012 and No. 201210171629.3 filed on May 29, 2012, which applications are incorporated herein by reference.

BACKGROUND OF THE PRESENT INVENTION

Field of Invention

The present invention relates to the field of biotechnology, in particular to a RTN4B-related polypeptide, a monoclonal antibody thereof, a monoclonal antibody-producing hybridoma cell strain, and, preparation and applications thereof.

Description of Related Arts

RTN4B belongs to reticolon family (RTNs), and is named for containing special endoplasmic reticulum localization, and has conserved RHD structure frame (reticulon-homology domain). The family contains four genes of RTN1, RTN2, RTN3 and RTN4, wherein many reports are about researching RTN4. RTN4 (also named as Nogo/ASY/RTN-X) gene has a plurality of alternative splicing isoforms, which mainly encode three proteins of RTN4A (GenBank Accession number AF148537), RTN4B (GenBank Accession number AF148538), and RTN4C (GenBank Accession number AF087901), while some other alternative splicing isoforms are mainly specifically expressed in testis.

RTN4B shows ubiquitous expression in normal tissues, and studies found that RTN4B is closely related to the occurrence and development of a tumor. Firstly, RTN4B involves in the apoptotic regulation of tumor cells. Tsujimoto et al found that RTN4B enables to interact with Bcl-2 and Bcl-xL, and recruits Bcl-2 and Bcl-xL to the endoplasmic reticulum, to reverse the inhibition effect of apoptosis of Bcl-2 and Bcl-xL. Yutsudo et al found that RTN4B appears transcriptional repression in the sample of small cell lung cancer, while overexpression of RTN4B may significantly promote the apoptosis of tumor cells. Secondly, recent reports further found that RTN4B may well be related with vascular remodeling, and even angiogenesis. In 2004, Acevedo, L et al found that RTN4B shows expression in vascular endothelial cells and smooth muscle cells of a mammal RTN4B recombinant protein may promote the migration of vascular endothelial cells and inhibit the migration of smooth muscle cells. Next, RTN4A/B knockout mice appear abnormal thickening blood vessel walls and shrunken vascular lumen after vascular injury. Again, re-import RTN4B into mice through adenoviral vector, the abnormal thickening blood vessel walls can be restored to normal morphology. Therefore, RTN4B may well be the key molecule for mammals to maintain the morphology of blood vessel and to regulate reconstruction of blood vessel. Subsequently, the group further identified the receptor molecule of RTN4B on the endothelial cell surface, NgBR. The knock-down experiment has proved that the interaction between NogoB and NgBR is requisite for VEGF blood-derived molecule to induce angiogenesis. Miao et al have further proved that the interaction between NogoB and NgBR enables to regulate angiogenesis by activating the Akt pathway in cells.

SUMMARY OF THE PRESENT INVENTION

The object of the present invention is to provide a RTN4B-related polypeptide, a monoclonal antibody thereof, a monoclonal antibody-producing hybridoma cell strain, and, preparation and applications thereof The first aspect of the present invention discloses an isolated RTN4B polypeptide, including an amino acid sequence presented by SEQ ID NO: 1 or its conservative variant polypeptide.

```
SEQ ID NO: 1: DEDEDLEELEVLERK.
```

The RTN4B polypeptide of the invention is designed on basis of RTN4B protein with a sequence of SEQ ID NO: 2. The isolated RTN4B polypeptide comprises at least a full length of Nos. 44-58 amino acid residues of RTN4B protein. The RTN4B protein has a full length of 373 amino acids, and its sequence is shown in SEQ ID NO: 2.

```
SEQ ID NO: 2 :
MEDLDQSPLVSSSDSPPRPQPAFKYQFVREPEDEEEEEEEEEDED
EDLEELEVLERKPAAGLSAAPVPTAPAAGAPLMDFGNDFVPPAPRG
PLPAAPPVAPERQPSWDPSPVSSTVPAPSPLSAAAVSPSKLPEDDE
PPARPPPPPPASVSPQAEPVWTPPAPAPAAPPSTPAAPKRRGSSGS
VVVDLLYWRDIKKTGVVFGASLFLLLSLTVFSIVSVTAYIALALLS
VTISFRIYKGVIQAIQKSDEGHPFRAYLESEVAISEELVQKYSNSA
LGHVNCTIKELRRLFLVDDLVDSLKFAVLMWVFTYVGALFNGLTLL
ILALISLFSVPVIYERHQAQIDHYLGLANKNVKDAMAKIQAKIPGL
KRKAE
```

As particularly recited in the embodiments of the invention, the amino acid sequence of the isolated RTN4B polypeptide is SEQ ID NO: 1. The monoclonal antibody prepared by hybridoma technology by using the RTN4B polypeptide, may recognize natural RTN4B protein, such that non full length fragments of RTN4B protein, given that containing SEQ ID NO: 1, may generate a monoclonal antibody for recognizing natural RTN4B protein. From the above, it is concluded that the RTN4B polypeptide may be a non full length fragment of RTN4B protein containing SEQ ID NO: 1. Preferably, the amount of amino acid residues of the non full length fragment of RTN4B protein is 15 to 27, preferably 15 to 23.

The second aspect of the present invention discloses an isolated polynucleotide, to encode the RTN4B polypeptide.

The polynucleotide may be used to construct a vector for expressing the RTN4B polypeptide, to prepare the RTN4B polypeptide.

Further, the polynucleotide may also be used as a target, for screening or preparing drugs or preparations related to the promotion or inhibition of the expression of RTN4B protein or RTN4B gene.

The active ingredient of the drugs or preparations related to the promotion or inhibition of the expression of RTN4B protein or RTN4B gene may be selected from, but not limited to: a nucleic acid molecule, a carbohydrate, a lipid, small molecule chemical drugs, antibody drugs, polypeptides, proteins or interference slow virus.

The third aspect of the present invention discloses a monoclonal antibody capable of specifically binding with the RTN4B polypeptide.

The monoclonal antibody can be obtained by using the RTN4B polypeptide as immunogen to immune mammals and to separate and obtain B cells, followed by prepare and screen by applying hybridoma technology to obtain hybridoma cell strains, which are further cultured under a suitable condition.

The mammal may be selected from a variety of common mammals, such as rats, rabbits, monkeys, pigs, human, etc.

The monoclonal antibody as particularly recited in the embodiments of the invention is generated by the hybridoma cell strain with an accession number of CGMCC NO. 5863 or its passage cell strains.

The monoclonal antibody may also be obtained by applying genetic engineering method by cloning the nucleotide encoding the heavy and light chains of the monoclonal antibody into a suitable vector and being expressed by introducing into a suitable host.

After obtaining the hybridoma cells by hybridoma technology, the full length and variable regional sequence of the heavy and light chains of the monoclonal antibody secretory expressed by the hybridoma cells can be analyzed and obtained by the conventional techniques in the art, thereby inferring encoding gene thereof, and then may construct engineered bacteria or engineered cells to express the monoclonal antibody by applying genetic engineering method and using a known sequence.

The engineering bacteria or engineering cells may be prokaryotic cells such as bacterial cells, or lower eukaryotic cells such as yeast cells, or higher eukaryotic cells such as mammalian cells. Representative examples include: *E. coli*, yeast, *lactobacillus, bifidobacterium, enterococcus, streptomyces*, plant cells, insect cells of *drosophila* S2 or Sf9, CHO, COs. 293 cells, etc.

Preferably, the monoclonal antibody includes a heavy chain and a light chain, wherein the amino acid sequence of the heavy chain variable region is SEQ ID NO: 3, the amino acid sequence of the light chain variable region is SEQ ID NO: 4.

The amino acid sequence of the heavy chain variable region (SEQ ID NO: 3):

PGASVKLSCKA<u>SGYTFTTYWINW</u>IKQRPGQGLEWIG<u>RIAPGSGSTY</u>

<u>YNEMFKS</u>KATLTVDTSSSTAY IQLSSLSSEDSAVYFC<u>ARDGMGYY</u>

<u>YGSRYWYFDV</u>WGAG

Wherein the Nos. 12-23 is CDR1 (first hypervariable region), the Nos. 37-55 is CDR2 (second hypervariable region), and the Nos. 85-101 is CDR3 (third hypervariable region).

The encoded amino acid sequence of the heavy chain variable region (SEQ ID NO: 5):

```
CCTGGGGCCT CAGTGAAGCT GTCCTGCAAG GCTTCTGGCT

ACACCTTCAC CACCTACTGG ATTAACTGGA TAAAACAGAG

GCCTGGACAG GGCCTTGAGT GGATAGGACA TATTGCTCCT
```

-continued
```
GGAAGTGGTA GTACTTACTA CAATGAAATG TTCAAGAGCA

AGGCAACACT GACTGTAGAC ACATCCTCCA GCACAGCCTA

CATTCAGCTC AGCAGCCTGT CATCTGAGGA CTCTGCTGTC

TATTTCTGTG CAAGAGATGG GATGGGATAT TACTACGGTA

GTAGGTACTG GTACTTCGAT GTCTGGGGCG CAGGG
```

The amino acid sequence of the light chain variable region (SEQ ID NO: 4):

ASLAVSLGQRATI<u>SCRASESVDNYGISFMNWF</u>QQKPGQPPKLLI<u>YAA</u>

<u>SNQGS</u>GVPARFSGSGSGTDFSLNI HPMEGDDSAMYF<u>CQQSKEV</u>

<u>PRTRS</u>EG

Wherein the Nos. 15-32 is CDR1, the Nos. 45-52 is CDR2, and the Nos. 84-94 is CDR3.

The encoded amino acid sequence of the light chain variable region (SEQ ID NO: 6):

```
GCTTCTTTGG CTGTGTCTCT AGGGCAGAGG GCCACCATCT

CCTGCAGAGC CAGCGAAAGT GTTGATAATT ATGGCATTAG

TTTTATGAAC TGGTTCCAAC AGAAACCAGG ACAGCCACCC

AAACTCCTCA TCTATGCTGC ATCCAACCAA GGATCCGGGG

TCCCTGCCAG GTTTAGTGGC AGTGGGTCTG GGACAGACTT

CAGCCTCAAC ATCCATCCTA TGGAGGGGGA TGATTCTGCA

ATGTATTTCT GTCAGCAAAG TAAGGAGGTT CCTCGTACAC

GTTCGGAGGG G
```

The monoclonal antibody may be a full length antibody, a Fab antibody, a chimeric antibody, a single chain antibody (ScFv), a F(ab)$_2$ antibody, a F(ab')$_2$ antibody, or other reshaping antibodies.

The monoclonal antibody may be PEGylation or non-PEGylation.

The fourth aspect of the present invention, discloses a hybridoma cell strain to produce the monoclonal antibody.

The hybridoma cell strain may be a rat-mouse hybridoma cell strain, a mouse-human hybridoma cell strain, a human-human hybridoma cell strain and the like.

The hybridoma cell strain is obtained by hybridoma technology by using the RTN4B polypeptide as an immunogen.

Preferably, the accession number of the hybridoma cell strain is CGMCC NO. 5863.

The strain was registration and preservation on Mar. 6, 2012 in the China General Microbiological Culture Collection Center (Address: 1 Beichen West Road, Chaoyang District Court No. 3), and accession number is CGMCC NO. 5863, classified name is: mouse hybridoma cell.

The fifth aspect of the present invention discloses a use of the RTN4B polypeptide, the monoclonal antibody or the hybridoma cell strain in the manufacture of drugs or preparations for the treatment, prevention or diagnosis of a tumor, or in the screening of drugs or preparations for the treatment or prevention of a tumor.

Specifically, the monoclonal antibody specifically binding with the RTN4B polypeptide and the hybridoma cell strain may be used to prepare drugs or preparations for the treatment or prevention of a tumor, the RTN4B polypeptide or the monoclonal antibody specifically binding with the RTN4B polypeptide may be used to prepare drugs or preparations for the diagnosis of a tumor, the RTN4B polypeptide or the monoclonal antibody specifically binding with the RTN4B polypeptide may be used for screening drugs or preparations for the treatment or prevention of a tumor.

The RTN4B polypeptide or the monoclonal antibody specifically binding with the RTN4B polypeptide being used for screening drugs or preparations for the treatment or prevention of a tumor refers to that: the RTN4B polypeptide or the monoclonal antibody is served as drugs or preparations to perform screening on the drugs or preparations by aiming at the target or comparative object of tumor cells, to search for the drugs capable for inhibiting or promoting RTN4B protein expression as candidate drugs of tumor treatment.

The RTN4B polypeptide and/or the monoclonal antibody specifically binding with the RTN4B polypeptide being used to prepare drugs or preparations for the diagnosis of a tumor refers to that: the RTN4B polypeptide and/or the monoclonal antibody specifically binding with the RTN4B polypeptide are used to prepare drugs or preparations for the diagnosis of a tumor with the RTN4B protein level as an indicator.

The fifth aspect of the present invention also discloses a method for treating or preventing tumors, which method is that administering the tumor cells with the monoclonal antibody specifically binding with the RTN4B polypeptide.

The tumor cell is selected from the tumor cells with its growth or proliferation related to the expression or activity of the RTN4B protein.

Further, the tumor is liver cancer, and the tumor cell is liver cancer cell.

The sixth aspect of the present invention, discloses a drug for treating or preventing tumors, the active ingredient of the drug comprises the monoclonal antibody specifically binding with the RTN4B polypeptide.

Further, the drug also includes a pharmaceutically acceptable excipient.

During the preparation of the drug, the active ingredient is commonly mixed with the excipient, or diluted with the excipient, or wrapped in a carrier in the form of a capsule or sachet. Examples of suitable excipient agent include: lactose, dextrose, sucrose, sorbitol, mannitol, starch, microcrystalline cellulose, polyvinylpyrrolidone, cellulose, water, etc. Preparation may further include: wetting agents, emulsifiers, preservatives (e.g., hydroxy benzoic acid methyl ester and propyl ester), sweeteners and the like.

The drug may take various common forms of troche, pill, powder, solution, syrup, sterile injected solution.

When the pharmaceutical composition is used for preventing or treating a tumor in vivo, the effective amount of the pharmaceutical composition is administered to the subject, i.e., refers to the amount of a known monoclonal antibody.

The seventh aspect of the present invention, discloses a tumor diagnostic agent, which contains the RTN4B polypeptide and/or the monoclonal antibody specifically binding with the RTN4B polypeptide.

The tumor diagnostic agent may be prepared by immune reaction principle, typically includes ELISA diagnostic reagents, colloidal gold diagnostic reagents, diagnostic reagents of light activation method, etc.

The present invention designs a RTN4B polypeptide on basis of the RTN4B protein sequence, and then, the synthesis of the polypeptide is followed by prepare and obtain a hybridoma cell strain capable for generating its specific monoclonal antibody by using the polypeptide, herein the hybridoma cell strain may stability secrete a monoclonal antibody of the RTN4B polypeptide, which has been proved to effectively block the growth of tumor cells in the nude mice subcutaneously, and is expected for clinical anti-tumor therapy. The invention further discloses various applications of the RTN4B polypeptide and the specific monoclonal antibody thereof, to lay the foundation for further expansion of related applications of the RTN4B protein.

DETAILED DESCRIPTION OF THE PREFERRED EMBODIMENTS

Figure 1:
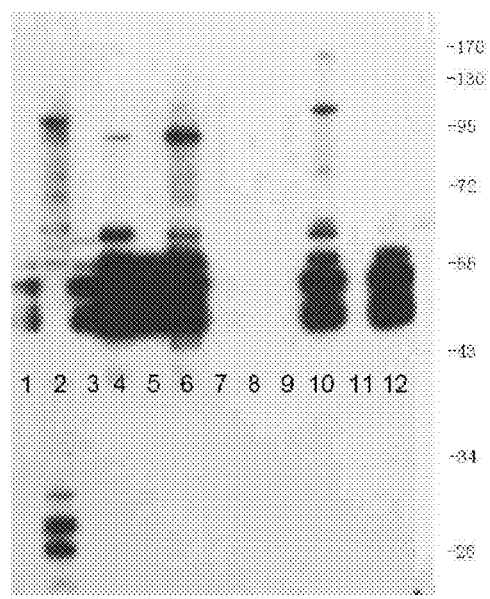
FIG. 1 is ELISA and Western blot results of the antibody.
9: 6F2
11: 1% milk-PBST
12: serum of immune mouse

Prior to the further description of specific embodiments of the present invention, it should be understood that the scope of the invention is not limited to the specific embodiments described below. It should also be understood that the terminology used in the examples of the invention is to describe the specific embodiments, but not intended to limit the scope of the present invention.

As giving numerical ranges in the embodiments, it should be understood that, unless otherwise specified in the invention, two endpoints of each numerical range and any numerical value between the two endpoints can be selected. Unless otherwise defined, all the technologies and scientific terms used in the invention have identical meanings with the commonly understanding of those skilled in the art. Besides the specific methods, apparatus and materials used in the embodiments, according to the grasp of the prior art and the records in the invention, those skilled in the art may accomplish the invention by the similar or equivalent method, apparatus and materials in the prior art with that in the embodiments of the invention.

Unless otherwise specified, the experimental method, detection method and preparation method disclosed in the invention apply the conventional techniques of molecular biology, biochemistry, chromatin structure and analysis, analytical chemistry, cell culture, recombinant DNA technology in the prior art or related fields. Those technologies are well described in the literature, and more details see Sambrook et al, MOLECULAR CLONING: A LABORATORY MANUAL, Second edition, Cold Spring Harbor Laboratory Press, 1989 and Third edition, 2001; Ausubel et al, CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolffe, eds.), Academic Press, San Diego, 1999; and METHODS IN MOLECULAR BIOLOGY, Vol. 119, Chromatin Protocols (P. B. Becker, ed.) Humana Press, Totowa, 1999, etc.

Example 1

Acquisition of a Hybridoma Cell Strain and Preparation of a Monoclonal Antibody 1 Materials and instruments 1.1 Cell Strain, Tissue Specimen and Animals a. myeloma cells (SP2/0)

b. BALB/C mice 1.2 Major Reagents a. Freund's complete adjuvant, Freund's incomplete adjuvant, HAT, HT, ABTS, PEG (molecular weight of 4000)

b. HRP labeled rabbit anti-mouse IgG c. RPMI 1640 culture: Hyclone Company d. nitrocellulose membrane (NC): Hybond Company e. calf serum: Hangzhou Evergreen Biological Engineering Materials Co., Ltd.

f. murine monoclonal antibody subclass typing kit g. coating buffer: composed of sodium carbonate 0.795 g and sodium bicarbonate 1.465 g diluting with every 500 ml of deionized water, PH value is 9.6.

h. substrate buffer: composed of disodium hydrogen phosphate 9.2 g and citric acid 2.55 g diluting with every 500 ml of deionized water, PH value is 5.0.

i. ABTS color solution: composed of ABTS 5 mg and 3% hydrogen peroxide 20 µl diluting with every 10 ml of substrate buffer.

j. 1640 cultivate stoste: composed of 1640 dry powder 5.2 g, β-mercaptoethanol 1.7 µl and HEPES 23.83 g diluting with every 500 ml of deionized water, PH value is adjusted by sodium hydroxide to 7.2.

k. incomplete 1640 cultivate solution: composed of 7.5% sodium bicarbonate 15 ml diluting with every 500 ml of 1640 cultivate stoste.

l. complete 1640 cultivate solution: composed of calf serum 20 ml diluting with every 80 ml of incomplete 1640 cultivate solution.

m: antibody diluents: composed of BSA 0.1 g diluting with every 100 ml of PBS.

n. wash Buffer: composed of Tween-20 0.5 ml diluting with every 100 ml of PBS.

o. PEG preparation solution: composed of DMSO 1 ml and 7.5% sodium bicarbonate 0.1 ml diluting with every 8.9 ml of incomplete 1640 cultivate solution.

1.3 Main Instruments a. carbon dioxide incubator: Forma Scientific Company;

b. super-clean bench: Suzhou Purification Equipment Instrument;

c. inverted microscope: Olympus Company d. 37° C. thermostatic water bath cauldron:

e. microtiter plates, cell culture plates: NUNC Company f. high-speed desktop centrifuge: Hunan Xiangya instrument factory g. nucleic acid protein detector:

h. pure water instrument: Millipore Company i. miniature vertical slab electrophoresis tank: Bio-Rad Company j. electrotransfer instrument: Bio-Rad Company 2 Method 2.1 Cell Cultivation: Myeloma Cells and Hybridoma Cells were Cultured in Complete 1640 Cultivate Solution, and Placed in 37° C., 5% Carbon Dioxide Incubator, Changed Liquid Every Other Day, and Passaged Once Every 3-4 Days.

2.2 Preparation of Antigen: Synthesize a Polypeptide with Sequence of SEQ ID NO: 1, and Take the Polypeptide as an Antigen to Immunize Mice.

2.3 Preparation of Monoclonal Antibody

The specific preparation process of monoclonal antibody is conducted referring to "Experimental Technology of Cellular and Molecular Immunology" Chapter II (Editor: JIN BoQuan, Fourth Military Medical University Press, 2001. 11, ISBN 7-81086-027-5), which is specifically described as follows:

2.3.1 Mice Immunization

BALB/C mice (4-8 weeks old, female) are immunized by the synthetic polypeptide (SEQ ID NO: 1), with specific steps as follows:

a. First immunization: polypeptide 500 µg per mouse, an equal volume of Freund's complete adjuvant is added and mixed, followed by multi-point injection subcutaneously with 1 ml per BALB/C mouse, and 0.2 ml per point with an interval of 3 weeks.

b. Second immunization: with the same dose and approach as above, while an equal volume of Freund's incomplete adjuvant was added, with an interval of 3 weeks.

c. Third immunization: ditto dose, no adjuvant, and use an equal volume of normal saline, intraperitoneal injection for BALB/C mice. 10 days later, tail veins of the immunized mice were extracted (collection followed by overnight at 4° C. in refrigerator, then centrifugated at 2000 rpm/min for 10 minutes the next day and the supernatant was reserved), and coated by RTN4B protein, and then serum titer thereof is detected through ELISA.

d. Fourth immunization: with the same dose and approach as the third immunization, the mice with serum titer greater than 1:10000 were intraperitoneal injected three days prior to fusion.

2. 3. 2 Procedure of ELISA Method for Detecting the Serum Titer of an Immunized Mouse:

a. One day before the detection, the RTN4B was diluted by the coating buffer to 1 µg/ml, and then added to the microtiter plate, with each hole of 100 µl, and overnight at 4° C. in a refrigerator;

b. The coated liquid within the microtiter plate was poured the next day, and washed with the washing buffer three times, and pat dry every time;

c. Separately add serums to be tested with PBS gradient dilution (serums: with each PBS of 1:100, 1:1000, 1:2000, 1:4000, 1:8000, 1:16000) with 100 µl per hole, take the serum of non-immunized BALB/C mouse as a negative control, and set in 37° C. thermostatic water bath cauldron for 1 hour.

d. The liquid within the microtiter plate was poured, and washed with the washing buffer three times, and pat dry every time;

e. HRP-labeled rabbit anti-mouse IgG antibody (dilution to 1:5000 by antibody diluent) was added with 100 µl per hole, and set in 37° C. thermostatic water bath cauldron for 1 hour.

f. The liquid within the microtiter plate was poured, and washed with the washing buffer three times, and pat dry every time;

g. Coloration, ABTS color solution of 100 µl (fresh) was added into each hole, and set in 37° C. thermostatic water bath cauldron for 10 to 15 minutes.

h. result detection: on a white background, directly observe the color in the reaction holes with the naked eye, that is the deeper the color is, the stronger the positive degree is, and negative reaction shows colorless or very light.

2. 3. 3 Preparation of Feeder Cells (Taking Mouse Peritoneal Macrophages One Day Prior to Fusion):

Take 6 weeks old female BALB/C mouse, which is sacrificed through cervical dislocation and soaked in 75% alcohol for disinfection of 5 minutes, then skin of the abdomen is cut with a sterile scissor to expose the peritoneum, then inject 8 ml incomplete 1640 cultivate solution each time by a sterile syringe, repeatedly wash, extract flushing fluid into a 50 ml centrifuge tube (total approximately 40 ml), and centrifugated at 1300 rpm /min for 5 minutes; after the supernatant was discarded, precipitate is resuspended by complete 1640 cultivate solution, to regulate the number of cells to $1\times10^5$ cells/ml, and cells are added into a 96-well plate with 100 μl per hole and cultivate in a 5% $CO_2$ culture box at 37° C.

2. 3. 4 Process of Cell Fusion

Observe the SP2/0 state of myeloma cells (requiring the best in logarithmic growth phase), preheat the prepared 45% PEG and 20 ml of incomplete 1640 culture solution into the cell incubator at 37° C. (the preparation of 45% PEG: the prepared 45% PEG was standby in the refrigerator at 4° C. one day prior to the fusion, PEG of 1 g was added into a penicillin vial and autoclaved to obtain a liquid of 0.9 ml, which further was added with 1.1 ml PEG preparation solution to obtain 45% PEG).

b. The SP2/0 cells were collected into a 50 ml sterile centrifuge tube and counted (the required total number of cells is $1\times10^6$), and then centrifuged at 1300 rpm/min for 7 minutes.

c. Prepare sterile dish, screen stencil, penicillin vial, BALB/C mice with sacrificial through cervical dislocation and four immunized and being soaked in 75% alcohol for 5 minutes.

d. The spleens of the immunized mice were removed under sterile conditions and into penicillin vials, the spleens was washed with 5 ml of incomplete 1640 culture solution and moved to a screen stencil (the screen stencil has been placed in a dish), added with about 40 ml incomplete 1640 culture solution, and grinded the spleens by a 5 ml sterile glass syringe stylet to fine, remove the grinding fluid into a 50 ml sterile centrifuge tube (cell count, the required total number of cells is $1\times10^7$), and then centrifuged at 1300 rpm/min for 7 minutes.

e. The supernatants of both SP2/0 cells by centrifugation and spleen cells are removed, the two kinds of cell precipitates are resuspended with incomplete 1640 cultivate solution, and then the two kinds of cells are mixed in a 50 ml sterile centrifuge tube, and centrifugated at 1300 rpm/min for 7 minutes.

f. The supernatant of the mixed cells are removed, followed by resuspend the cell precipitate with incomplete 1640 cultivate solution, and centrifugated at 1300 rpm/min for 7 minutes.

h. Remove the supernatant of the mixed cells, and keep the mouth of the centrifuge tube downward, and blott residual liquid;

i. Flick the bottom of the centrifuge tube, to slightly loose the cell precipitate;

j. At room temperature, the preheating 45% PEG is added along the tube wall within 30 seconds and stirred gently, followed by extracted into a 1 ml pipette and is stand for 90 seconds;

k. The liquid in the pipette is gently dropped into the bottom of the centrifuge tube, and is terminated with the preheating incomplete 1640 culture solution: 1 ml incomplete 1640 culture solution is absorbed and added along the tube wall within 2 minutes; subsequently, added with a speed of 1 ml per minute for 2 minutes, followed by 2 ml per minute for 2 minutes, and 4 ml per minute till reaching total 20 ml incomplete 1640 culture solution, then centrifuged at 800 rpm/min for 6 minutes.

l. Remove the supernatant, then the precipitation is gently mixed with 6 ml 1640 complete culture solution, followed by add the complete culture solution to about 40 ml;

m. the fused cell suspension is added to the 96-walls plate containing feeder cells, with 100 μl per hole, at 37° C. and cultivate in a 5% $CO_2$ culture box.

2. 3. 5 Selection of Hybridomas

Add selected culture solution after the fusion for 24 hours, with specific process as follows:

a. After the fusion for 24 hours, HAT 1.6 ml and HT 0.4 ml are added to 20 ml complete 1640 culture solution, and then added to a 96-well plate with 50 μl per hole;

b. Change liquid after 2 days, and after absorbing 150 μl from each hole within the 96-well plate, the proposed complete 1640 culture solution is added (compose of complete 1640 culture solution with HAT 0.6 ml and HT 0.6 ml per 60 ml)

c. Change liquid after another 2 days, and after absorbing 150 μl from each hole within the 96-well plate, the proposed complete 1640 culture solution is added (compose of complete 1640 culture solution with HT 1.2 ml per 60 ml)

d. Detecting the hybridoma supernatants by ELISA method 2 days later: one day before the detection, the RTN4B was diluted by the coating buffer to 1 μg/ml, and then added to the microtiter plate, with each hole of 100 μl, and overnight at 4° C. in a refrigerator. The next day, wash the coating plate with the washing buffer three times, and pat dry every time. Add the supernatant within the 96-well plate, respectively, and take the serum of non-immunized BALB/C mouse as a negative control, take the serum of a mouse with titer greater than 1:10000 as a positive control, and set in 37° C. thermostatic water bath cauldron for 1 hour. Wash the coating plate with the washing buffer three times, and pat dry every time. HRP-labeled rabbit anti-mouse IgG antibody was added into each hole, which is further diluted by the antibody diluents to 1:5000, and set in 37° C. thermostatic water bath cauldron for 1 hour. Wash the coating plate with the washing buffer three times, and pat dry every time. ABTS color solution of 100 μl was added into each hole, and set in 37° C. thermostatic water bath cauldron for 10 to 15 minutes. Result detection: on a white background, directly observe the color in the reaction holes with the naked eye, that is the deeper the color is, the stronger the positive degree is, and negative reaction shows colorless or very light.

f. Mark positive holes, and choose the cells in the positive holes to perform cloning.

2.3. 6 Cloning, Enlarging Cultivation and Cryopreservation of Hybridomas

The cloning of the hybridoma is performed by limited dilution method, with the specific approach as follows:

a. Preparation of feeder cell suspension (spleen cell suspension): the non-immunized BALB/C mouse is sacrificed through cervical dislocation and soaked in 75% alcohol for disinfection of 5 minutes, remove the spleen of mouse under sterile conditions into a penicillin vial, after washing with 5 ml incomplete 1640 cultivate solution, the spleen is moved to a screen stencil (the screen stencil has been placed in a dish), added with about 20 ml incomplete 1640 culture solution, and grinded the spleens by a 5 ml sterile glass syringe stylet to fine, then remove the grinding fluid into a sterile glass bottle, add the complete 1640 culture solution to 80 ml followed by add 3.2 ml HT and mix. The mixed suspension is added into the 96-walls plate, respectively, 100 μl per hole, and the last three holes at the lower right corner of each plate (H10, H11, H12) without any feeder cell suspension is prepared for attenuation, the added plate is placed at 37° C. and cultivate in a 5% $CO_2$ culture box.

b. The cells in the holes to be cloning are suspended (softly blow and beat by a 200 μl pipette) and counted, the cell suspension is moved to the dilution hole H10 of the plate with feeder cells, and 20 μl cell suspension in the hole H10 is removed to the hole H11 and is 10-fold diluted by complete 1640 culture solution, then 20 μl cell suspension in the hole H11 is removed to the hole H12 and is 10-fold diluted by complete 1640 culture solution.

c. Diluting the cell suspension in the hole H12 by complete 1640 culture solution to theoretically 1 cell per 100 μl, then respectively drop the dilution liquid in the 96-walls plate with feeder cell suspension (each hole is diluted followed by drop into 48 holes), each hole is 100 μl, and is set at 37° C. and cultivate in a 5% $CO_2$ culture box.

d. One week later, mark the monoclonal hole, and detect the supernatant in monoclonal hole by ELISA method (same as 2. 5. 2. d), choose the cells in positive hole to perform the next cloning. After three time repeatedly, the hybridoma capable of secreting monoclonal antibody stably (all the monoclonal holes of the next cloning of the cell performing cloning are positive) is obtained.

f. Select the cells with strongest positive in the monoclonal hole to be cultured in a 24-walls plate (1 hole to 1 hole), and divide into 2 holes within the 24-walls plate three days later, then divide into 4 holes another three days later, then another 2 days later, the cells in the 4 holes are moved to a 50 ml cell culture flask for enlarging cultivation.

g. cryopreservation of hybridoma cells: after the cells in the 50 ml cell culture flask covers the bottom area with approximately 70%, the cells in the culture flask are blown and beat by a pipet to be completely suspended, then the cell suspension is moved to a 50 ml sterile centrifuge tube and counted, and then centrifugated at 1200 rpm/min for 6 minutes. Remove supernatant, and resuspend the precipitate with a cell freezing medium (50% of calf serum, 40% of incomplete 1640 cultivate solution and 10% of DMSO) and regulate the cell density to $1 \times 10^7$/ml. Separate in freezing Tubes, with 1 ml per tube, and set in a 4° C. refrigerator for 1 hour, then move to a −20° C. refrigerator for 2 hour, then move to a −70° C. refrigerator overnight, the next day move the freezing cells into a liquid nitrogen tank for storing.

The obtained hybridoma cell strain is deposited, with the accession number of CGMCC NO. 5863, labeled as 6F2.

Example 2

Preparation of Recombinant Monoclonal Antibody

Obtain sequences of both heavy chain variable region and light chain variable region.
1. Cultivation and collection of hybridoma cells
2. Extraction of total RNA of hybridoma cells by a conventional method
3. Reverse transcription of RNA to CDNA
4. Take the prepared CDNA as a template, and perform conventional PCR amplification to obtain sequences of the heavy chain and light chain variable regions
5. The detection shows that the amino acid sequence of the heavy chain variable region is SEQ ID NO: 3, the coding sequence of the heavy chain variable region is SEQ ID NO: 5, the amino acid sequence of the light chain variable region is SEQ ID NO: 4, the coding sequence of the light chain variable region is SEQ ID NO: 6.

6. After obtaining the coding sequences of the heavy chain and light chain variable regions by sequencing, through the total synthesis or splicing PCR method, the heavy, light chain Fab genes with restriction sites on both sides are obtained according to the known sequences of heavy and light chain constant regions of a mouse.

7. The obtained heavy, light chain Fab genes are inserted into the expression vector pGP1, to constitute the expression vector of Fab antibody. The expression vector also may be vectors of phCMV-II, pcDNA3.1 or pCI-Neo, etc.

8. After identified correctly, the constructed expression vector of Fab antibody transfects CHO cells according to conventional methods. The transfection CHO cells perform monocloning after cultivation. ELISA method is used to respectively detect the expression of antibodies, and to select the clones with higher expression for the preparation of expression products of Fab antibody.

Detailed method of the preparation of the above recombinant monoclonal antibodies may also see reference (Cloning immunoglobulin variable domains for expression by the polymerase chain reaction Proc. Natl. Acad. Sci. USA Vol. 86, pp. 3833-3837, May 1989, Medical Sciences).

The similar method may also be used to prepare recombinant full-length antibodies or recombinant chimeric antibodies with the constant region of human or mouse.

Example 3

Mass Production and Functional Analysis of Monoclonal Antibody

Apply the hybridoma cells with an amount of $1 \times 10^6$ cells per mouse to intraperitoneal inject the 8-10 week old female BALB/C mice, which has been previously sensitized by liquid paraffin. 10-14 days later, collect ascites, and coated by RTN4B protein (refer to the preparation in ZL00111791.2). Detect the ascites positive through ELISA (results are as shown in table 1), and the ascites used for western blotting method is proved to enable to recognize RTN4B protein; meanwhile, the ascites used for immunohistochemical is prove to enable to recognize natural RTN4B protein, with the results as shown in table 1. The monoclonal antibody secreted by the hybridoma cell strain lays the foundation for further research of new gene RTN4B.

TABLE 1

| Concentration of antigen | ELISA results (OD450 value) | | | |
|---|---|---|---|---|
| | 100 ng/hole | 10 ng/hole | 1 ng/hole | 0.1 ng/hole |
| 6F2 | 3.289 | 2.667 | 0.448 | 0.093 |
| PC | 3.415 | 3.001 | 1.156 | 0.371 |
| NC | 0.044 | 0.043 | 0.053 | 0.043 |

6F2: ascites obtained by a mouse after the inoculation of hybridoma cells CGMCC NO. 5863
PC (positive control): serum of immune mouse (obtained by step 2. 3. 1)
NC (blank control): 5% milk-PBS

Example 4

Anti-Tumor Test of Monoclonal Antibody

Experimental Steps:
1. Apply hepatoma cells SMMC7721, and culture the cells. Collect the cells, which are further diluted to a cell suspension with a concentration of $2\times10^7$.
2. Inoculate nude mice by SMMC7721 cell suspension subcutaneously, wherein each mouse is inoculated with 200 ul.
3. The mouse is inoculated with hepatoma cells CGMCC NO. 5863 to obtain ascites, which is purified by a common affinity column, and further dialyzed to normal saline after the purification, and then filtered by a 0.2 um filter membrane to obtain monoclonal antibody injection with the monoclonal antibody concentration of 2 ug/ul.
4. Inject the monoclonal antibody injection as prepared in step 3 the next day after the cell inoculation. Divide animals into four groups: normal saline group, negative antibody (mouse anti-human IgG (purchased from Shanghai enzyme-linked biological), positive avastin group, and experimental group 6F2 (injected with monoclonal antibody injection as prepared in step 3), 8 for each group.

Figure 2:
FIG. 2 is results of anti tumor test on animals
Figure 3:
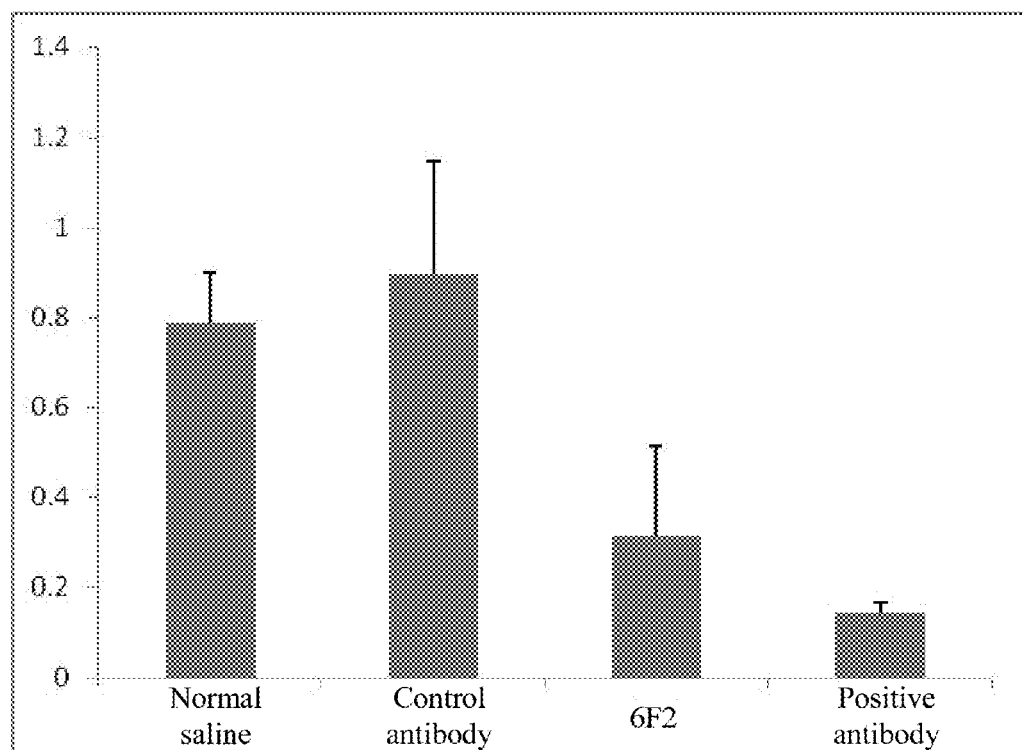
FIG. 3 is weight charts of tumors of anti tumor test on animals
Ordinate represents: total weight of tumor, unit: g
Control antibody is a negative control mouse anti-human IgG, positive antibody is avastin.
P value (normal saline VS control antibody): 0.288297
P value (6F2 VS control antibody): 0.000168
P value (positive antibody VS control antibody): 0.000058

Dose:
Normal saline group: 100 ul/each
Negative antibody 1B2 group: 200 ug antibody/100 ul/each Positive avastin group: 200 ug/100 ul/each
Experimental group 6F2: 200 ug (by weight in monoclonal antibody of injection)/100 ul/each.
5. Twice injections a week, and continuous inoculation for four weeks.
6. Take and photograph tumors 4 weeks later, with the results as shown in FIG. 2, 3. From the results, one can see that the size of tumors in normal saline group and negative control 1B2 group have no difference. The tumor size of positive control AVASTIN group features much smaller than that of negative control group. While the experimental group 6F2 features less effect of tumor inhibition than that of positive drugs, but obvious effect of tumor inhibition than that of the negative control.

Conclusion: results show that, compared to the control antibody with no blocking, the monoclonal antibody 6F2 of the invention can significantly inhibit the growth of liver cancer cells SMMC-7721 in nude mice, and is expected to be used for clinical anti-tumor therapy.

The above are only preferred embodiments of the present invention, which are not restricted to any form and substance of the present invention. It should be pointed out that, for the ordinary skill in the art, without departing from the premise of the method of the present invention, several improvements and supplements may be made, while such improvements and supplements are deemed to be the scope of the present invention. For those skilled technical personnel in the art, without departing from the spirit and scope of the present invention, the equal changes of minor modifications, embellishments and evolutions made by using the above disclosed technical content are equivalent embodiments of the present invention; meanwhile, any equivalent changes of modifications, embellishments and evolutions related to above embodiments on basis of the substantive technology of the invention, are belong to the scope of the technical solution of the present invention.

---

What is claimed is:

1. A monoclonal antibody capable of specifically binding with the RTN4B polypeptide comprising a heavy chain and a light chain, the amino acid sequence of the heavy chain variable region is SEQ ID No: 3, the amino acid sequence of the light chain variable region is SEQ ID No: 4.

2. The monoclonal antibody according to claim 1, characterized in that, the monoclonal antibody is PEGylation or non-PEGylation.

3. The monoclonal antibody according to claim 1, characterized in that, the monoclonal antibody is a full length antibody, a Fab antibody, a chimeric antibody, a single chain antibody, a F(ab)$_2$ antibody, a F(ab')$_2$ antibody.

4. A drug for treating tumors comprising the active ingredient of the drug comprises the monoclonal antibody as in claim 1.

5. The drug according to claim 4, characterized in that, the monoclonal antibody is generated by the hybridoma cell strain with an accession number of CGMCC NO. 5863.

6. The drug according to claim 4, characterized in that, the monoclonal antibody comprises a heavy chain and a light chain, the amino acid sequence of the heavy chain variable region is SEQ ID NO: 3, the amino acid sequence of the light chain variable region is SEQ ID NO: 4.

7. A tumor diagnostic agent, which comprises the monoclonal antibody as in claim 1.

8. A tumor diagnostic kit, which comprises the monoclonal antibody of claim 1.

9. The tumor diagnostic kit according to claim 8, characterized in that, the monoclonal antibody is generated by the hybridoma cell strain with an accession number of CGMCC NO. 5863.

10. The tumor diagnostic kit according to claim 8, characterized in that, the monoclonal antibody comprises a heavy chain and a light chain, the amino acid sequence of the heavy chain variable region is SEQ ID NO: 3, the amino acid sequence of the light chain variable region is SEQ ID NO: 4.

11. The monoclonal antibody according to claim 1, characterized in that, the monoclonal antibody is generated by the hybridoma cell strain with an accession number of CGMCC NO. 5863.

12. A tumor diagnostic kit, which comprises a monoclonal antibody of claim 11.

13. A hybridoma cell strain to produce the monoclonal antibody as in claim 1.

14. The hybridoma cell strain according to claim 13, characterized in that, the accession number is CGMCC NO. 5863.

* * * * *

SEQUENCE LISTING

```
<160> NUMBER OF SEQ ID NOS: 6

<210> SEQ ID NO 1
<211> LENGTH: 15
<212> TYPE: PRT
<213> ORGANISM: Homo sapiens

<400> SEQUENCE: 1

Asp Glu Asp Glu Asp Leu Glu Glu Leu Glu Val Leu Glu Arg Lys
1               5                   10                  15

<210> SEQ ID NO 2
<211> LENGTH: 373
<212> TYPE: PRT
<213> ORGANISM: Homo sapiens

<400> SEQUENCE: 2

Met Glu Asp Leu Asp Gln Ser Pro Leu Val Ser Ser Ser Asp Ser Pro
1               5                   10                  15

Pro Arg Pro Gln Pro Ala Phe Lys Tyr Gln Phe Val Arg Glu Pro Glu
            20                  25                  30

Asp Glu Glu Glu Glu Glu Glu Glu Glu Glu Asp Glu Asp Glu Asp
        35                  40                  45

Leu Glu Glu Leu Glu Val Leu Glu Arg Lys Pro Ala Ala Gly Leu Ser
    50                  55                  60

Ala Ala Pro Val Pro Thr Ala Pro Ala Ala Gly Ala Pro Leu Met Asp
65                  70                  75                  80

Phe Gly Asn Asp Phe Val Pro Pro Ala Pro Arg Gly Pro Leu Pro Ala
                85                  90                  95
```

```
Ala Pro Pro Val Ala Pro Glu Arg Gln Pro Ser Trp Asp Pro Ser Pro
            100                 105                 110

Val Ser Ser Thr Val Pro Ala Pro Ser Pro Leu Ser Ala Ala Ala Val
            115                 120                 125

Ser Pro Ser Lys Leu Pro Glu Asp Asp Glu Pro Pro Ala Arg Pro Pro
            130                 135                 140

Pro Pro Pro Pro Ala Ser Val Ser Pro Gln Ala Glu Pro Val Trp Thr
145                 150                 155                 160

Pro Pro Ala Pro Ala Pro Ala Ala Pro Pro Ser Thr Pro Ala Ala Pro
            165                 170                 175

Lys Arg Arg Gly Ser Ser Gly Ser Val Val Asp Leu Leu Tyr Trp
            180                 185                 190

Arg Asp Ile Lys Lys Thr Gly Val Val Phe Gly Ala Ser Leu Phe Leu
            195                 200                 205

Leu Leu Ser Leu Thr Val Phe Ser Ile Val Ser Val Thr Ala Tyr Ile
            210                 215                 220

Ala Leu Ala Leu Leu Ser Val Thr Ile Ser Phe Arg Ile Tyr Lys Gly
225                 230                 235                 240

Val Ile Gln Ala Ile Gln Lys Ser Asp Glu Gly His Pro Phe Arg Ala
            245                 250                 255

Tyr Leu Glu Ser Glu Val Ala Ile Ser Glu Glu Leu Val Gln Lys Tyr
            260                 265                 270

Ser Asn Ser Ala Leu Gly His Val Asn Cys Thr Ile Lys Glu Leu Arg
            275                 280                 285

Arg Leu Phe Leu Val Asp Asp Leu Val Asp Ser Leu Lys Phe Ala Val
            290                 295                 300

Leu Met Trp Val Phe Thr Tyr Val Gly Ala Leu Phe Asn Gly Leu Thr
305                 310                 315                 320

Leu Leu Ile Leu Ala Leu Ile Ser Leu Phe Ser Val Pro Val Ile Tyr
            325                 330                 335

Glu Arg His Gln Ala Gln Ile Asp His Tyr Leu Gly Leu Ala Asn Lys
            340                 345                 350

Asn Val Lys Asp Ala Met Ala Lys Ile Gln Ala Lys Ile Pro Gly Leu
            355                 360                 365

Lys Arg Lys Ala Glu
    370

<210> SEQ ID NO 3
<211> LENGTH: 105
<212> TYPE: PRT
<213> ORGANISM: artificial sequence
<220> FEATURE:
<223> OTHER INFORMATION: amino acid sequence of the heavy chain variable
      region of the monoclonal antibody

<400> SEQUENCE: 3

Pro Gly Ala Ser Val Lys Leu Ser Cys Lys Ala Ser Gly Tyr Thr Phe
1               5                   10                  15

Thr Thr Tyr Trp Ile Asn Trp Ile Lys Gln Arg Pro Gly Gln Gly Leu
            20                  25                  30

Glu Trp Ile Gly Arg Ile Ala Pro Gly Ser Gly Ser Thr Tyr Tyr Asn
            35                  40                  45

Glu Met Phe Lys Ser Lys Ala Thr Leu Thr Val Asp Thr Ser Ser Ser
50                  55                  60

Thr Ala Tyr Ile Gln Leu Ser Ser Leu Ser Ser Glu Asp Ser Ala Val
```

```
                65                  70                  75                  80
Tyr Phe Cys Ala Arg Asp Gly Met Gly Tyr Tyr Tyr Gly Ser Arg Tyr
                    85                  90                  95

Trp Tyr Phe Asp Val Trp Gly Ala Gly
                100                 105

<210> SEQ ID NO 4
<211> LENGTH: 97
<212> TYPE: PRT
<213> ORGANISM: artificial sequence
<220> FEATURE:
<223> OTHER INFORMATION: amino acid sequence of the light chain variable
      region of the monoclonal antibody

<400> SEQUENCE: 4

Ala Ser Leu Ala Val Ser Leu Gly Gln Arg Ala Thr Ile Ser Cys Arg
1               5                   10                  15

Ala Ser Glu Ser Val Asp Asn Tyr Gly Ile Ser Phe Met Asn Trp Phe
                20                  25                  30

Gln Gln Lys Pro Gly Gln Pro Pro Lys Leu Leu Ile Tyr Ala Ala Ser
            35                  40                  45

Asn Gln Gly Ser Gly Val Pro Ala Arg Phe Ser Gly Ser Gly Ser Gly
        50                  55                  60

Thr Asp Phe Ser Leu Asn Ile His Pro Met Glu Gly Asp Asp Ser Ala
65                  70                  75                  80

Met Tyr Phe Cys Gln Gln Ser Lys Glu Val Pro Arg Thr Arg Ser Glu
                85                  90                  95

Gly

<210> SEQ ID NO 5
<211> LENGTH: 315
<212> TYPE: DNA
<213> ORGANISM: artificial sequence
<220> FEATURE:
<223> OTHER INFORMATION: nucleotide sequence of the heavy chain variable
      region of the monoclonal antibody

<400> SEQUENCE: 5 cctgggggcct cagtgaagct gtcctgcaag gcttctggct acaccttcac cacctactgg     60
attaactgga taaaacagag gcctggacag ggccttgagt ggataggacg tattgctcct    120
ggaagtggta gtacttacta caatgaaatg ttcaagagca aggcaacact gactgtagac    180
acatcctcca gcacagccta cattcagctc agcagcctgt catctgagga ctctgctgtc    240
tatttctgtg caagagatgg gatgggatat tactacggta gtaggtactg gtacttcgat    300
gtctggggcg caggg                                                    315

<210> SEQ ID NO 6
<211> LENGTH: 291
<212> TYPE: DNA
<213> ORGANISM: artificial sequence
<220> FEATURE:
<223> OTHER INFORMATION: nucleotide sequence of the light chain variable
      region of the monoclonal antibody

<400> SEQUENCE: 6
gcttctttgg ctgtgtctct agggcagagg gccaccatct cctgcagagc cagcgaaagt     60
gttgataatt atggcattag tttttatgaac tggttccaac agaaaccagg acagccaccc   120
aaactcctca tctatgctgc atccaaccaa ggatccgggg tccctgccag gtttagtggc   180
```

```
agtgggtctg ggacagactt cagcctcaac atccatccta tggaggggga tgattctgca    240
atgtatttct gtcagcaaag taaggaggtt cctcgtacac gttcggaggg g              291
```